United States Patent
Devonport et al.

(10) Patent No.: US 7,071,261 B2
(45) Date of Patent: Jul. 4, 2006

(54) AQUEOUS COMPOSITION CONTAINING POLYMERIC NANOPARTICLES

(75) Inventors: Wayne Devonport, Doylestown, PA (US); Ralph Craig Even, Blue Bell, PA (US); Ann Robertson Hermes, Ambler, PA (US); Dennis Paul Lorah, Lansdale, PA (US); Joseph David Tanzer, Fort Washington, PA (US); Antony Keith VanDyk, Blue Bell, PA (US)

(73) Assignee: Rohm and Haas Company, Philadelphia, PA (US)

( * ) Notice: Subject to any disclaimer, the term of this patent is extended or adjusted under 35 U.S.C. 154(b) by 247 days.

(21) Appl. No.: 10/461,952

(22) Filed: Jun. 13, 2003

(65) Prior Publication Data

US 2003/0232914 A1    Dec. 18, 2003

Related U.S. Application Data

(60) Provisional application No. 60/414,601, filed on Sep. 30, 2002, provisional application No. 60/389,043, filed on Jun. 14, 2002.

(51) Int. Cl.
*C08L 39/00* (2006.01)
*C08L 33/14* (2006.01)

(52) U.S. Cl. ............. 524/555; 524/556; 524/560; 524/525; 524/502; 524/515

(58) Field of Classification Search ............ 524/556, 524/560, 525, 502, 515, 555
See application file for complete search history.

(56) References Cited

U.S. PATENT DOCUMENTS

| | | | | |
|---|---|---|---|---|
| 4,560,714 A | * | 12/1985 | Gajria et al. | 523/409 |
| 5,212,273 A | | 5/1993 | Das et al. | 526/323.1 |
| 5,270,380 A | | 12/1993 | Adamson et al. | |
| 5,804,627 A | | 9/1998 | Landy et al. | |
| 5,861,188 A | * | 1/1999 | Schall et al. | 427/137 |
| 5,863,996 A | | 1/1999 | Graham | 526/216 |
| 5,874,111 A | * | 2/1999 | Maitra et al. | 424/499 |
| 5,922,398 A | | 7/1999 | Hermes et al. | |
| 6,130,014 A | * | 10/2000 | Yau et al. | 430/14 |
| 6,268,222 B1 | | 7/2001 | Chandler et al. | 436/523 |
| 6,329,446 B1 | | 12/2001 | Sacripante et al. | 523/161 |
| 6,420,023 B1 | * | 7/2002 | Rowley et al. | 428/355 CN |
| 2002/0065208 A1 | | 5/2002 | Aubay et al. | 510/475 |
| 2003/0059599 A1 | | 3/2003 | Beckley et al. | |

FOREIGN PATENT DOCUMENTS

| | | |
|---|---|---|
| EP | 0114 478 | 8/1984 |
| EP | 0 644 205 | 8/1994 |
| WO | WO 93/00376 | 1/1993 |
| WO | WO 93/24534 | 12/1993 |
| WO | WO 9324534 A1 * | 12/1993 |
| WO | WO 01/43859 | 7/1998 |
| WO | WO 99/01522 | 1/1999 |
| WO | WO 00/59951 | 10/2000 |
| WO | WO 00/68316 | 11/2000 |
| WO | WO 00/75244 | 12/2000 |
| WO | WO 01/90226 | 11/2001 |
| WO | WO 02/26895 | 4/2002 |
| WO | WO 02/32982 | 4/2002 |
| WO | WO 200226895 A1 * | 4/2002 |

OTHER PUBLICATIONS

Copending Application 10/461,954; 10/461,949; 10/461,958; 10/461,963.*

Dieter Horn and Jens Rieger, "Organic Nanoparticles in the Aqeous Phase—Theory, Experiment, and Use", Agnew, Chem. Int. Ed. 2001, 40, pp. 4330-4361.

* cited by examiner

*Primary Examiner*—David W. Wu
*Assistant Examiner*—Satya Sastri
(74) *Attorney, Agent, or Firm*—Kim R. Jessum; Ronald D. Bakule

(57) ABSTRACT

An aqueous composition including an aqueous dispersion of polymeric nanoparticles having a mean diameter of from 1 to 50 nanometers, the particles including, as polymerized units, at least one multi-ethylenically-unsaturated monomer and at least one ethylenically unsaturated water soluble monomer is discloseded. Certain embodiments of the composition include pigment particles and other polymer particles. The aqueous compositions include aqueous coating compositions.

1 Claim, No Drawings

AQUEOUS COMPOSITION CONTAINING POLYMERIC NANOPARTICLES

CROSS REFERENCE TO RELATED PATENT APPLICATIONS

This is a non-provisional application of prior pending U.S. provisional application Ser. 60/389,043 filed on Jun. 14, 2002 and provisional application Ser. No. 60/414,601 filed on Sep. 30, 2002.

This invention relates to an aqueous composition. In particular, this invention relates to an aqueous composition including an aqueous dispersion of polymeric nanoparticles (PNPs) having a mean diameter of from 1 to 50 nanometers (nm), the particles including as polymerized units at least one multi-ethylenically-unsaturated monomer and at least one water soluble monomer. This invention also relates to aqueous coating compositions including PNPs.

"Coatings" herein include compositions to be applied to various substrates and commonly identified as architectural coatings such as, for example, flat coatings, semigloss coatings, gloss coatings, primers, topcoats, stain-blocking coatings, penetrating sealers for porous substrates such as chalky surfaces, concrete, and marble, elastomeric coatings, mastics, caulks, and sealants; industrial coatings such as, for example, board and panelling coatings, transportation coatings, furniture coatings, and coil coatings; maintenance coatings such as, for example, bridge and tank coatings and road marking paints; leather coatings and treatments; floor care coatings; paper coatings; personal care coatings such as for hair, skin, nails, woven and nonwoven fabric coatings and pigment printing pastes; printing materials such as, for example, inks and overprint varnishes; and adhesive coatings such as, for example, pressure sensitive adhesives and wet- and dry-laminating adhesives. Aqueous coating compositions having improved open time, improved coating stability, improved freeze/thaw stability, and improved setting time have long been sought. By "improved" properties herein is meant that the properties are improved relative to those of corresponding aqueous coating compositions in which the PNPs are replaced by an equal weight of polymeric particles of the same composition having a mean diameter of greater than 50 nm.

Published PCT Patent Application WO 99/01522 discloses a coating composition including a crosslinking agent and polymeric particles having a mean particle diameter most preferably between about 20 and about 40 nm formed in the presence of the reaction product of one or more carboxylic fatty acids and ammonia or one or more polyfunctional aromatic or aliphatic amines, the dried composition providing a water resistant wood coating.

It is still desired to provide alternative aqueous compositions with at least one improved property as described herein. It has now been found that such improvements are provided in aqueous coating compositions which include an aqueous dispersion of polymeric particles having a mean diameter of 1 to 50 nm, the particles including as polymerized units at least one multi-ethylenically-unsaturated monomer and at least one water soluble monomer.

In a first aspect of the present invention there is provided an aqueous composition comprising an aqueous dispersion of PNPs having a mean diameter of from 1 to 50 nm, said nanoparticles comprising, as polymerized units, at least one multi-ethylenically-unsaturated monomer and at least one ethylenically unsaturated water soluble monomer.

In a second aspect of the present invention there is provided an aqueous composition comprising an aqueous dispersion of first polymeric particles that are PNPs having a mean diameter of from 1 to 50 nm, said first particles comprising, as polymerized units, at least one multi-ethylenically-unsaturated monomer and at least one ethylenically unsaturated water soluble monomer; and an aqueous dispersion of second polymeric particles having a mean diameter of greater than 50 nm.

In a third aspect of the present invention there is provided an aqueous composition comprising a pigment, an aqueous dispersion of PNPs having a mean diameter of 1 to 50 nm, said particles including amine functionality and further including, as polymerized units, at least one multi-ethylenically-unsaturated monomer; an anionically-stabilized emulsion polymer having a mean diameter of greater than 50 nm; and a volatile base in an amount sufficient to deprotonate the amine.

In a fourth aspect of the present invention there is provided an aqueous composition including a pigment and an aqueous dispersion of PNPs having a mean diameter of 1 to 50 nm, said particles comprising, as polymerized units, at least one multi-ethylenically unsaturated monomer and at least 2% by weight, based on the weight of said particles, ionic ethylenically unsaturated monomer.

The aqueous composition of the present invention includes an aqueous dispersion of polymeric particles having a mean diameter in the range of from 1 to 50 nm, the particles including, as polymerized units, at least one multiethylenically unsaturated monomer and at least one ethylenically unsaturated water soluble monomer. As used herein, the term "dispersion" refers to a physical state of matter that includes at least two distinct phases wherein a first phase is distributed in a second phase, the second phase being a continuous medium. By "aqueous" herein is meant a medium that is from 50 to 100 weight % water, based on the weight of the aqueous medium.

The PNPs are addition polymers which contain, as polymerized units, at least one multiethylenically unsaturated monomer and at least one ethylenically unsaturated water soluble monomer. Suitable multiethylenically unsaturated monomers useful in the present invention include di-, tri-, tetra-, or higher multifunctional ethylenically unsaturated monomers, such as, for example, divinyl benzene, trivinylbenzene, divinyltoluene, divinylpyridine, divinylnaphthalene divinylxylene, ethyleneglycol di(meth)acrylate, trimethylolpropane tri(meth)acrylate, diethyleneglycol divinyl ether, trivinylcyclohexane, allyl (meth)acrylate, diethyleneglycol di(meth)acrylate, propylene glycol di(meth)acrylate, 2,2-dimethylpropane-1,3-di(meth)acrylate, 1,3-butylene glycol di(meth)acrylate, 1,4-butanediol di(meth)acrylate, 1,6-hexanediol di(meth)acrylate, tripropylene glycol di(meth)acrylate, triethylene glycol di(meth)acrylate, tetraethylene glycol di(meth)acrylate, polyethylene glycol di(meth)acrylates, such as polyethylene glycol 200 di(meth)acrylate and polyethylene glycol 600 di(meth)acrylate, ethoxylated bisphenol A di(meth)acrylate, poly(butanediol)

di(meth)acrylate, pentaerythritol tri(meth)acrylate, trimethylolpropane triethoxy tri(meth)acrylate, glyceryl propoxy tri(meth)acrylate, pentaerythritol tetra(meth)acrylate, dipentaerythritol monohydroxypenta(meth)acrylate, divinyl silane, trivinyl silane, dimethyl divinyl silane, divinyl methyl silane, methyl trivinyl silane, diphenyl divinyl silane, divinyl phenyl silane, trivinyl phenyl silane, divinyl methyl phenyl silane, tetravinyl silane, dimethyl vinyl disiloxane, poly(methyl vinyl siloxane), poly(vinyl hydro siloxane), poly(phenyl vinyl siloxane), and mixtures thereof. The term "(meth)acrylic" includes both acrylic and methacrylic and the term "(meth)acrylate" includes both acrylate and methacrylate. Likewise, the term "(meth)acrylamide" refers to both acrylamide and methacrylamide. "Alkyl" includes straight chain, branched and cyclic alkyl groups.

Typically, the PNPs contain at least 1% by weight based on the weight of the PNPs, of at least one polymerized multiethylenically unsaturated monomer. Up to and including 99.5 weight % polymerized multiethylenically unsaturated monomer, based on the weight of the PNPs, is effectively used in the particles of the present invention. It is preferred that the amount of polymerized multiethylenically unsaturated monomer is from 1% to 80%, more preferably from 1% to 60%, most preferably from 1% to 25%, by weight based on the weight of the PNPs.

The PNPs further contain, as polymerized units, at least one water soluble monomer. By "water soluble monomer" herein is meant a monomer having a solubility in water of at least 7 weight %, preferably at least 9 weight %, and most preferably as least 12 weight %, at a temperature of 25° C. Data for the water solubility of monomers is found, for example, in "Polymer Handbook" (Second Edition, J. Brandrup, E. H. Immergut, Editors, John Wiley & Sons, New York) and "Merck Index" (Eleventh Edition, Merck & Co, Inc., Rahway, N.J.). Examples of water soluble monomers include ethylenically unsaturated ionic monomers and ethylenically unsaturated water soluble nonionic monomers. Typically, the amount of the polymerized water soluble monomer is at least 0.5 weight %, based on the weight of the PNPs. Up to and including 99 weight % polymerized water soluble monomer, based on the weight of the PNPs, can be effectively used in the particles of the present invention.

Ethylenically unsaturated ionic monomer, referred to herein as "ionic monomer" is a monomer that is capable of bearing an ionic charge in the aqueous medium in which the PNPs are dispersed. Suitable ionic monomers include, for example, acid-containing monomers, base-containing monomers, amphoteric monomers; quaternized nitrogen-containing monomers, and other monomers that can be subsequently formed into ionic monomers, such as monomers which can be neutralized by an acid-base reaction to form an ionic monomer. Suitable acid groups include carboxylic acid groups and strong acid groups, such as phosphorus containing acids and sulfur containing acids. Suitable base groups include amines. It is preferred that the amount of polymerized ionic monomer based on the weight of the PNPs is in the range from 0.5 to 99 weight %, more preferably in the range of from 1 to 50 weight %, even more preferably from 2 to 40 weight %, and most preferably from 3 to 25 weight %.

Suitable carboxylic acid-containing monomers include carboxylic acid monomers, such as (meth)acrylic acid, acryloxypropionic acid, and crotonic acid; dicarboxylic acid monomers, such as itaconic acid, maleic acid, fumaric acid, and citraconic acid; and monomers which are half esters of dicarboxylic acids, such as monomers containing one carboxylic acid functionality and one $C_{1-6}$ ester. Preferred are acrylic acid and methacrylic acid. Suitable strong acid monomers include sulfur acid monomers, such as 2-acrylamido-2-methyl propane sulfonic acid, styrene sulfonic acid, vinyl sulfonic acid, sulfoethyl (meth)acrylate, sulfopropyl (meth)acrylate, 2-acrylamido-2-methyl propane sulfinic acid, styrene sulfinic acid, and vinyl sulfinic acid; and phosphorus acid monomers, such as 2-phosphoethyl (meth)acrylate, vinyl phosphoric acid, and vinyl phosphinic acid. Other acid monomers include terminally unsaturated acid containing macromonomers as disclosed in U.S. Pat. No. 5,710,227. Phosphorus acid monomers are desirable as they can provide improved adhesion to certain substrates (e.g., metal).

Suitable base-containing monomers include monomers having amine functionality, which includes N,N-dimethylaminoethyl (meth)acrylate, N,N-diethylaminoethyl (meth) acrylate, N-t-butylaminoethyl (meth)acrylate, N,N-dimethylaminopropyl (meth)acrylamide, p-aminostyrene, N,N-cyclohexylallylamine, allylamine, diallylamine, dimethylallylamine, N-ethyldimethylallylamine, crotyl amines, and N-ethylmethallylamine; monomers having pyridine functionality, which includes 2-vinylpyridine and 4-vinylpyridine; monomers having piperidine functionality, such as vinylpiperidines; and monomers having imidazole functionality, which includes vinyl imidazole. Other suitable base-containing monomers include oxazolidinylethyl (meth) acrylate, vinylbenzylamines, vinylphenylamines, substituted diallylamines, 2-morpholinoethyl (meth)acrylate, methacrylamidopropyl trimethyl ammonium chloride, diallyl dimethyl ammonium chloride, 2-trimethyl ammonium ethyl methacrylic chloride, and the like.

Suitable amphoteric monomers include N-vinylimidazolium sulfonate inner salts and N,N-Dimethyl-N-(3-methacrylamidopropyl)-N-(3-sulfopropyl) ammonium betaine.

Suitable functional monomers, in which the functionality is subsequently formed into an acid or base include monomers containing: an epoxide functionality, such as glycidyl (meth)acrylate and allyl glycidyl ether; an anhydride, such as maleic anhydride; an ester such as methyl acrylate; and a halide. Suitable halide-containing functional monomers include vinylaromatic halides and halo-alkyl(meth)acrylates. Suitable vinylaromatic halides include vinylbenzyl chloride and vinylbenzyl bromide. Other suitable functional monomers include allyl chloride, allyl bromide, and (meth) acrylic acid chloride. Suitable halo-alkyl(meth)acrylates include chloromethyl (meth)acrylate. Suitable functional monomers, in which the functionality is subsequently forming into a nonionic water soluble group include vinyl acetate. Hydrolysis of the polymerized vinyl acetate provides hydroxyl groups to the PNPs.

Multiethylenically unsaturated monomers that are also water soluble monomers are alternatively used to prepare the PNPs. In such embodiments, these monomers are classified for the purposes of the present invention as both a multiethylenically unsaturated monomer and a water soluble monomer. An example of a water soluble, multiethylenically unsaturated monomer is phosphodi(ethyl methacrylate).

Ethylenically unsaturated water soluble nonionic monomers are referred to herein as "water soluble nonionic monomers". Examples of water soluble nonionic monomers include hydroxyalkyl (meth)acrylates such as hydroxyethyl (meth)acrylate and hydroxypropyl (meth)acrylate; poly (alkylene oxide) esters of (meth)acrylic acid such as poly (ethylene oxide)$_{20}$ methacrylate and poly(propylene oxide)$_{150}$ acrylate; acrylamide; and methacrylamide. It is preferred that the amount of polymerized water soluble nonionic monomer based on the weight of the PNPs is in the range from 0.5 to 99 weight %, more preferably in the range of from 20 to 90 weight %, even more preferably from 30 to 80 weight %, and most preferably from 40 to 70 weight %. When the PNPs include, as polymerized units, ionic monomer and nonionic water soluble monomer, lower levels of polymerized nonionic water soluble monomer are preferred.

The PNPs optionally contain, as polymerized units, one or more third monomers that are not multiethylenically unsaturated monomers and are not water soluble monomers. Suitable third monomers include $C_1$–$C_{24}$ alkyl (meth)acrylates, such as methyl (meth)acrylate, ethyl (meth)acrylate, propyl (meth)acrylate, butyl (meth)acrylate, isobutyl (meth) acrylate, hexyl (meth)acrylate, cyclohexyl (meth)acrylate, 2-ethylhexyl (meth)acrylate, octyl (meth)acrylate, decyl (meth)acrylate, dodecyl (meth)acrylate, pentadecyl (meth) acrylate, hexadecyl (meth)acrylate, octadecyl (meth)acrylate, and nonadecyl (meth)acrylate, and mixtures thereof. Other suitable third monomers include vinyl acetate; vinyl versatate; diisobutylene; ureido containing monomers such as N-(ethyleneureidoethyl)-4-pentenamide, N-(ethylenethioureido-ethyl)-10-undecenamide, butyl ethyleneureidoethyl fumarate, methyl ethyleneureido-ethyl fumarate, benzyl N-(ethyleneureido-ethyl) fumarate, and benzyl N-(ethyleneureido-ethyl) maleamate; vinylaromatic monomers, such as styrene, α-methylstyrene, vinyltoluene, p-methylstyrene, ethylvinylbenzene, vinylnaphthalene, vinylxylenes, and nonylphenoxy propenyl polyethoxylated alcohol. The vinylaromatic monomers also include their corresponding substituted counterparts, such as halogenated derivatives, i.e., containing one or more halogen groups, such as fluorine, chlorine or bromine; and nitro, cyano, ($C_1$–$C_{10}$) alkoxy, halo($C_1$–$C_{10}$)alkyl, ($C_1$–$C_{10}$)alkoxy, carboxy, and the like.

The PNPs have a mean diameter in the range of from 1 to 50 nm, preferably in the range of from 1 to 40 nm, more preferably from 1 to 30 nm, even more preferably from 1 to 25 nm, even further preferably from 1 to 20 nm, and most preferably from 1 to 10 nm. It is further typical that the PNPs have a mean particle diameter of at least 1.5 nm, preferably at least 2 nm. One method of determining the particle sizes (mean particle diameter) of the PNPs is by using standard dynamic light scattering techniques, wherein the correlation functions are converted to hydrodynamic sizes using LaPlace inversion methods, such as CONTIN.

Typically, PNPs including as polymerized units, less than 10 weight % multiethylenically unsaturated monomer, have a glass transition temperature from −90° C. to 170° C. for the composition in the absence of the polymerized multiethylenically unsaturated monomer, as determined by a modulated differential scanning calorimetry measurement. PNPs containing as polymerized units, at least 50 weight % multiethylenically unsaturated monomer are considered to have glass transition temperatures of at least 50° C.

The PNPs of the present invention typically have an "apparent weight average molecular weight" in the range of 5,000 to 1,000,000, preferably in the range of 10,000 to 500,000 and more preferably in the range of 15,000 to 100,000. As used herein, "apparent weight average molecular weight" reflects the size of the PNP particles using standard gel permeation chromatography methods, e.g., using THF solvent at 40° C., 3 PIgel™ Columns (Polymer Labs, Amherst, Mass.), 100 Angstrom (10 nm), $10^3$ Angstroms (100 nm), $10^4$ Angstroms (1 micron), 30 cm long, 7.8 mm ID, 1 milliliter per minute, 100 microliter injection volume, calibrated to narrow polystyrene standards using Polymer Labs CALIBRE™ software.

The PNPs are optionally characterized as having suitable hydrophilicities that allow the PNPs to be dispersed into an aqueous medium. One method to characterize the hydrophilicity of the PNPs is to calculate the Hansch parameter. The Hansch parameter is calculated using a group contribution method. The monomer units forming the polymer are assigned a hydrophobicity contribution and the relative hydrophobicity of the polymer is calculated based on the weight average of the monomers in the polymer. Hansch and Fujita, *J. Amer. Chem. Soc.*, 86, 1616–1626 (1964); H. Kubinyi, *Methods and Principles of Medicinal Chemistry*, Volume 1, R. Mannhold et al., Eds., VCH, Weinheim (1993); C. Hansch and A. Leo, *Substituent Constants for Correlation Analysis in Chemistry and Biology*, Wiley, New York (1979); and C. Hansch, P. Maloney, T. Fujita, and R. Muir, *Nature*, 194. 178–180 (1962).

Values of the hydrophobicity contributions for several monomers are listed in Table 1.

TABLE 1

| Monomer | Hydrophobicity Contribution |
| --- | --- |
| ethyl acrylate | 2.11 |
| butyl acrylate | 3.19 |
| 2-ethyl hexylacrylate | 5.22 |
| styrene | 4.29 |
| methyl methacrylate | 1.89 |
| ethyl methacrylate | 2.43 |
| butyl methacrylate | 3.51 |
| isobornyl methacrylate | 5.0 |
| butadiene | 4.0 |
| acrylic acid (high pH) | −2.52 |
| methacrylic acid (high pH) | −2.2 |
| maleic anhydride | −3.5 |

PNPs typically have a Hansch parameter in the range of from −2.5 to 4.0, preferably from −1.0 to 3.0.

The PNPs optionally contain other functional groups, which are provided by the polymerization of monomers containing those groups such as, for example, methylolated amides and silanols, or precursor groups thereof. Functional groups are optionally attached to the PNPs by reacting the ionic group of the PNP with a suitable compound. For example, PNPs containing carboxylic acid groups are modified to contain pendant hydrophilic groups by reacting carboxylic acid groups with a suitable alcohol, such as a capped polyalkylene oxide. Alternatively, functional groups are affixed to the PNPs through non-radical reactions resulting in the formation of ionic or covalent bonds between a modifying compound containing the groups and complementary reactable groups covalently bound to the PNP as taught in U.S. Pat. No. 5,270,380.

The complementary reactable groups in the PNP and modifying compound provide ionic or covalent bonding. Complementary ionic bonding includes acid-base interaction and ion pair bonding of negatively and positively charged atoms. Covalent bonding by complementary reactable groups includes, for example: (a) acetoacetate-aldehyde; (b) acetoacetate-amine; c) amine-aldehyde; (d) amine-anhydride; (e) amine-isocyanate; (f) amine-epoxy; (g) aldehyde-hydrazide; (i) acid-epoxy; (j) acid-carbodiimide; (k) acid-chloro methyl ester; (j) acid-chloro methyl amine; (m) acid-anhydride; (n) acid-aziridine; (o) epoxy-mercaptan; and (p) isocyanate-alcohol. The first or second reactable group in each pair is present either in the PNP or, alternatively, in the modifying compound.

A suitable method to prepare the aqueous composition containing the PNPs dispersed in an aqueous medium includes the steps of preparing a nonaqueous PNP dispersion containing the PNPs dispersed in at least one solvent; and combining the nonaqueous PNP dispersion with an aqueous medium. By "nonaqueous" herein is meant a medium that contains from zero to less than 50 weight % water, based on the weight of the nonaqueous medium. Aqueous compositions containing PNPs that include, as polymerized units, ionic monomers, are optionally partially or completely neutralized prior to, during, or after combining with the aqueous medium.

A suitable polymerization process to prepare the nonaqueous PNP dispersion is free radical solution polymerization of at least one multiethylenically unsaturated monomer, at least one water soluble monomer, and, optionally, at least one third monomer. By "solution polymerization" herein is meant free radical addition polymerization in a suitable solvent for the polymer. By "suitable solvent for the polymer" herein is meant that linear random (co)-polymers having substantially similar polymerized monomer units to the PNPs, are soluble in the solvent. Another method for selecting a suitable solvent or mixture of solvents is on the basis of using solubility parameter analysis. According to such methods, the suitability of the solvent is determined by substantially matching the solubility parameters of the PNP and of the solvent, such as the Van Krevelen parameters of delta d, delta p, delta h and delta v. See, for example, Van Krevelen et al., *Properties of Polymers. Their Estimation and Correlation with Chemical Structure*, Elsevier Scientific Publishing Co., 1976; Olabisi et al., *Polymer-Polymer Miscibility*, Academic Press, NY, 1979; Coleman et al., *Specific Interactions and the Miscibility of Polymer Blends*, Technomic, 1991; and A. F. M. Barton, *CRC Handbook of Solubility Parameters and Other Cohesion Parameters*, $2^{nd}$ Ed., CRC Press, 1991. Delta d is a measure of dispersive interactions, delta p is a measure of polar interactions, delta h is a measure of hydrogen bonding interactions, and delta v is a measure of both dispersive and polar interactions.

Such solubility parameters are alternatively calculated, such as by the group contribution method, or determined experimentally, as is known in the art. A preferred solvent has a delta v parameter within 5 (joule per cubic centimeter)$^{1/2}$, preferably within 1 (joule per cubic centimeter)$^{1/2}$ of the polymer delta v parameter. Suitable solvents for the polymerization include organic solvents, such as hydrocarbons; alkanes; halohydrocarbons; chlorinated, fluorinated, and brominated hydrocarbons; aromatic hydrocarbons; ethers; ketones; esters; alcohols; and mixtures thereof. Particularly suitable solvents, depending on the composition of the PNP, include dodecane, mesitylene, xylenes, diphenyl ether, gamma-butyrolactone, ethyl acetate, ethyl lactate, propyleneglycol monomethyl ether acetate, caprolactone, 2-heptanone, methylisobutyl ketone, acetone, methyl ethyl ketone, diisobutylketone, propyleneglycol monomethyl ether, alkyl-alcohols, such as isopropanol, decanol, and t-butanol; and supercritical carbon dioxide.

The nonaqueous PNP dispersion is prepared by first charging a solvent, or alternatively, a mixture of solvent and some portion of the monomers, to a reaction vessel. The monomer charge is typically composed of monomers, an initiator, and a chain transfer agent. Typically, initiation temperatures are in the range of from 55° C. to 125° C., although lower or higher initiator temperatures are possible using suitable low temperature or high temperature initiators known in the art. After the heel charge has reached a temperature sufficient to initiate polymerization, the monomer charge or balance of the monomer charge is added to the reaction vessel. The monomer charge time period is typically in the range of from 15 minutes to 4 hours. During the monomer charge, the reaction temperature is typically kept constant, although it is possible to vary the reaction temperature. After completing the monomer mixture addition, additional initiator in solvent can be charged to the reaction and/or the reaction mixture may be held for a time.

Control of PNP particle size and distribution is achieved by one or more of such methods as choice of solvent, choice of initiator, total solids level, initiator level, type and amount of multi-functional monomer, type and amount of ionic monomer, type and amount of chain transfer agent, and reaction conditions.

Initiators useful in the free radical polymerization of the present invention include, for example, one or more of: peroxyesters, alkylhydroperoxides, dialkylperoxides, azoinitiators, persulfates, redox initiators and the like. The amount of the free radical initiator used is typically from 0.05 to 10% by weight, based on the weight of total monomer. Chain transfer reagents are optionally used to control the extent of polymerization of the PNPs useful in the present invention. Suitable chain transfer agents include, for example: alkyl mercaptans, such as dodecyl mercaptan; aromatic hydrocarbons with activated hydrogens, such as toluene; and alkyl halides, such as bromotrichloroethane.

In one method of preparing the aqueous composition of the present invention, at least a portion of the polymerized ionic monomer units of the PNPs are neutralized with at least one neutralizing agent to form an at least partially neutralized nonaqueous PNP dispersion. The polymerized ionic monomer units of the PNPs can be neutralized in a variety of ways. When the polymerized ionic monomer units are acidic, the neutralizing agent is typically a base. Likewise, when the polymerized ionic monomer units are basic, the neutralizing agent is typically an acid. Suitable bases include inorganic and organic bases. Suitable inorganic bases include the full range of the hydroxide, carbonate, bicarbonate, and acetate bases of alkali or alkaline metals. Suitable organic bases include ammonia, primary/secondary/tertiary amines, diamines, and triamines. Preferred basic neutralizing agents include sodium hydroxide, and ammonium hydroxide. Suitable acids include carboxylic acids, such as acetic acid; dicarboxylic acids; (di)carboxylic/hydroxyl acids; aromatic acids, such as benzoic acid; and a variety of other acids, such as boric, carbonic, citric, iodic, nitrous, nitric, periodic, phosphoric, phosphorous, sulfuric, sulfurous, and hydrochloric acid. None of the foregoing categories of bases and acids, are deemed to be limiting.

The amount of neutralizing agent required to neutralize the nonaqueous PNP dispersion is typically determined on a molar basis of neutralizing agent to polymerized ionic monomer units of the PNPs. Without being bound to a particular theory, the amount of polymerized ionic monomer units (i.e., level of charge) needed to stabilize the PNPs (i.e., maintain particle size during conversion from non-aqueous to aqueous medium) will vary as PNP composition and properties are varied. It is believed that the PNP hydrophobicity, Tg, crosslinking level, and type of counter-ion from the neutralizing agent are important variables. For providing stable aqueous PNP dispersions (i.e., wherein flocculation of the PNPs is minimized), the polymerized ionic monomer units are preferably at least 20%, more preferably at least 50%, even more preferably at least 80%, and most preferably at least 90% neutralized.

Neutralizing the PNPs is alternatively carried out in a variety of ways. In one method, the nonaqueous PNP dispersion is added to a solution containing the neutralizing agent while stirring. Preferably, the neutralizing agent is added as an aqueous solution over time while stirring the nonaqueous PNP dispersion to provide an at least partially neutralized nonaqueous PNP dispersion.

In one method of preparing the aqueous composition containing dispersed PNPs, the at least partially neutralized nonaqueous PNP dispersion is combined with an aqueous medium. The aqueous medium optionally contains the neutralizing agent(s) for neutralizing the PNPs, in which case the nonaqueous PNP dispersion is capable of being simultaneously neutralized and combined with an aqueous medium. The aqueous medium optionally contains surfactants, which are capable of altering the stability of the PNPs, or of altering other properties of the resulting aqueous PNP dispersion, such as its surface tension.

The sequence of admixing the partially neutralized nonaqueous PNP dispersion and the aqueous medium is not critical. Various methods and equipment, which are suitable for mixing are described in *The Chemical Engineer's Handbook, 5th Edition*, Perry and Chilton, Eds., McGraw-Hill, Ch. 21, 1973. Typically, the aqueous medium is continuously stirred while adding the partially neutralized nonaqueous PNP dispersion to it in order to ensure that the solvent is intimately mixed with the aqueous medium, which minimizes flocculation of the PNPs.

Suitable weight percentages of the PNPs in the aqueous composition, based on total weight of the aqueous composition, are typically from 1 to 90 weight %, more typically from 2 to 75 weight %, even more typically from 4 to 65 weight %, further more typically from 8 to 55 weight %, and most typically from 10 to 45 weight %.

While the preparation of the aqueous composition of the present invention does not require the use of surfactants, and it is typical that the nonaqueous PNP dispersions are substantially free of surfactants, surfactants are optionally included. When present, the amount of surfactants is typically less than 3 weight percent, more typically less than 2 weight percent, even more typically less than 1 weight percent, further typically less than 0.5 weight percent, and even further typically less than 0.2 weight percent, based on total weight of the PNPs.

The aqueous composition is optionally treated to remove at least a portion of the solvent and, in some cases, water, to increase the solids content of the PNPs. Suitable methods to concentrate the PNPs include distillation processes, such as forming azeotropes of water and a suitable solvent; evaporation of solvent or water; drying the aqueous composition by freeze drying or spray drying; solvent extraction techniques; and ultrafiltration techniques. Preferably at least 25 weight %, more preferably at least 50 weight %, even more preferably at least 75 weight %, and most preferably 100 weight % of the solvent is exchanged with water. Removal of the solvent is preferably carried out under conditions that minimize destabilization (i.e., flocculation) of the PNPs.

In an alternative method, the aqueous composition of this invention is prepared by a method including the steps of preparing a nonaqueous PNP dispersion containing the PNPs dispersed in at least one solvent that is both a suitable solvent for the PNPs and is compatible or miscible in water; and combining the nonaqueous PNP dispersion with an aqueous medium. Examples of such suitable solvents for acrylic-containing PNPs, which are also compatible or miscible with water, include isopropanol and ether alcohols (e.g., monobutyl ether of ethylene glycol and monoethyl ether of diethylene glycol). In this method, the PNPs do not require the addition of neutralizing agents to impart particle stability when combined with water.

Alternative embodiments of the aqueous compositions of the present invention have a wide range of PNP content. Typically, the PNP weight fractions range from 0.1 to 99 weight %, more typically from 1 to 90 weight %, even more typically from 2 to 75 weight %, further typically from 5 to 50 weight %, and most typically 10 to 40 weight %, based on the weight of the aqueous composition.

The aqueous compositions of the present invention optionally contain other polymer particles that are not PNPs, such as emulsion polymer particles having a mean particle diameter of greater than 50 nm. The PNPs are present in the aqueous composition at a level of from 0.1 to 100 weight % PNPs based on the total weight of the polymer particles in the aqueous composition. The functional role of the PNPs determines the level of PNPs present. Some of the functional roles of the PNPs are, for example, as additives, as co-binders, as principal binders, and as sole binders. The amount of PNPs utilized ranges from a lower level for the former to a higher level of the latter.

In one embodiment, the PNPs are provided with other polymer particles, wherein the other polymer particles are prepared in the presence of the PNPs. In such embodiments the other polymer particles are typically prepared by emulsion polymerization in the presence of PNPs. Without being bound by a particular theory it is believed that the PNPs act as a stabilizer of the emulsion polymer particles, potentially minimizing or eliminating the need for the use of conventional surfactants in the polymerization process. In this embodiment, the PNPs are present in the aqueous composition at a level of from 1 to 99 weight %, preferably from 5 to 90 weight %, more preferably from 10 to 60 weight %, and most preferably from 20 to 60 weight %, based on the total weight of polymer in the aqueous composition.

In some embodiments the aqueous composition is subsequently applied to a substrate such as, for example, plastic including sheets and films, wood, metal, leather, woven and nonwoven fabrics, hair, skin, nails, paper, previously painted surfaces, cementitious substrates, and asphaltic substrates, with or without a prior substrate treatment such as a primer. The coating on the substrate is typically dried, or allowed to dry, at temperatures from 10° C. to 200° C.

In one embodiment of the present invention an aqueous composition including an aqueous dispersion of first particles that are PNPs having a mean diameter of 1 to 50 nm, the first particles including, as polymerized units, at least one multi-ethylenically-unsaturated monomer and at least one ethylenically unsaturated water soluble monomer and an aqueous dispersion of second polymeric particles having a mean diameter of greater than 50 nm is provided. Such aqueous compositions include aqueous coating compositions. Such aqueous compositions provide longer open time relative to corresponding aqueous compositions in which the PNPs are replaced by an equal weight of polymeric particles of the same composition having a mean diameter of greater than 50 nm.

Aqueous compositions containing an aqueous dispersion of second polymeric particles having a mean diameter of greater than 50 nm such as paints, stains, adhesives, overprint varnishes and printing inks dry quickly compared to solvent-borne compositions such as alkyd paints. Due to the fast drying nature of aqueous coatings, however, there is often not enough time to rebrush over the freshly coated wet surface to improve its appearance or to apply additional paint onto the freshly coated wet surface without causing defects such as brush marks, loss of gloss, or lap lines in the final dried coating. A "lap" as used herein, refers to an area on a substrate where additional coating is applied onto a portion of a previously coated, but still wet, adjacent substrate area. In the case of paint, it is desirable to seamlessly join up the edges of a wet painted area with newly added fresh paint without any visible lap showing in the dried coating. "Lapping" or "to lap" refers to the ability to do this seamless joining of edges without leaving a visible "lap" line. In the case of inks and overprint varnishes the related problems are premature drying on the press, redeposition of dry particulates on the prints and cleanup of the press.

As used herein, "open time" or "wet edge time" refers to the time that a coating remains workable, after it has been applied to a substrate, to allow for rebrushing or "melting in" of the newly applied coating at the lap, without resulting in the above defects. Open time is a more apparent problem in cases such as with sheen and gloss paints, i.e, aqueous coating compositions further including at least one pigment present at a level of pigment volume concentration ("PVC") lower than 35%, because a glossy appearance makes the surface defects in the dried coating more visible.

The conventional practice for addressing the quick drying nature of aqueous coatings has been to add substantial levels of water-soluble solvents, such as for example, 10% to 20% by weight based on total liquid weight, of polyethylene glycol or polypropylene glycol to such coatings to increase the open time. However, these solvents negate the desirable advantages of aqueous coatings such as safety, low tack, low odor, and low pollution. The aqueous dispersions of second polymeric particles having a mean diameter of greater than 50 nm are preferably aqueous emulsion polymers, typically polymers prepared by emulsion polymerization. In some embodiments the second polymer particles are prepared by a single or multi-stage emulsion polymerization process resulting in individual particles that are either uniform or are composed of two or more phases of various geometries. Such polymer particles typically have a weight average molecular weight in the range of from 75,000 to greater than 2,000,000; preferably in the range of from 90,000 to 1,500,000; and more preferably in the range of from 100,000 to 1,000,000. The weight average molecular weight of the second polymer particles is measured by gel permeation chromatography using a polymethylmethacrylate equivalent. The particle sizes of the second polymer particles typically have average particle diameters in the range of greater than 50 to 1000 nm, preferably from 70 to 300 nm. Particle sizes herein are those determined using a Brookhaven Model BI-90 particle sizer, reported as "effective diameter". Also contemplated are multimodal particle size emulsion polymers wherein two or more distinct particle sizes or very broad distributions are provided.

The second polymer particles are further characterized by having a glass transition temperature (Tg) in the range of −40° C. to 60° C. Tg, as used herein, means the temperature calculated by the Fox equation (Bulletin of the American Physical Society 1, 3, page 123 (1956)). Tg values for homopolymers are found, for example, in "Polymer Handbook", ed. by J. Brandrup and E. H. Immergut, Interscience Publishers. More preferred second polymer particles are those capable of forming a film at room temperature without the addition of a coalescent or another film forming aid. Film forming refers to the ability of the polymer particles to coalesce to form a film that is materially uniform. In embodiments wherein the particles contain a single pahse the polymer typically has a Tg range from −20° C. to 30° C.

Preferred second polymer particles include compositions that contain: from 70 to 99.7% by weight of a monoethylenically unsaturated monomer, from 0.3 to 10% by weight of a monoethylenically unsaturated acid monomer, and from 0 to 29% by weight of one or more monoethylenically unsaturated functional monomer. Multi-ethylenically unsaturated monomer in included in some embodiments.

In one embodiment at least some of the PNPs in paint formulations form a barrier layer at the air/coating interface while the paint is in the wet state. In this aspect of the invention, without being bound by a particular theory, PNPs are envisioned to function similarly to molecular monolayers for controlling the evaporation of water as is taught in Retardation of Evaporation by Monolayers: Transport Processes, La Met, Victor K.; Academic Press, New York (1962)). This barrier layer acts to slow the evaporation of water from the coating formulation, delaying the events that cause poor open time. In a preferred mode of this embodiment, the PNPs are individually stable in the paint formulation, i.e. they do not substantially adsorb onto the surfaces of other components of the paint formulation such as second polymer particles, pigments or fillers, nor do they aggregate, flocculate, or coagulate with themselves to form large masses.

In another embodiment, the stabilizing moieties strongly affixed to PNPs are hydrophilic and show a strong attraction to water. Whether or not the evaporation of water is slowed down, this attraction will lead to a hydrated layer around the binder that will oppose the forces that tend to coagulate the binder and give an increase in open time of the coatings system. The nature of the PNP and binder compositions envisioned in this embodiment is similar to that of the above use as a monolayer.

In the embodiment of the invention in which longer open time as defined hereinabove is particularly desired, a PNP including a copolymerized ethylenically unsaturated functional monomer as disclosed hereinabove is preferred. The functional monomer is alternatively a water soluble monomer or a third monomer. The functional monomer is introduced into the PNP prior to, during, or after the free radical polymerization to form the PNP. In embodiments where the copolymerized functional monomer is formed by post-functionalization of a precursor having a first reactable group with a modifying compound, the PNP includes at least one reactable group. More preferably, the PNP has a reactable ionizable acid group such as, for example, acrylic, methacrylic, itaconic, aconitic, citraconic, crotonic, maleic, fumaric, the dimer of acrylic acid, vinyl sulfonic acid, acrylamide-2-methylpropanesulfonic acid, phosphonoethyl methacrylate, and sulfonoethyl methacrylate. The modifying compound typically contains at least one hydrophilic group which includes, for example, hydroxy, polyoxyethylene, polyvinyl alcohol, polyacrylamide, poly-N-vinyl pyrrolidone, and natural polymers such as starch. The modifying compound must also contain a second reactable group which is complementary to the first reactable group in the PNP. In addition, the modifying compound may contain more than one complementary reactable group. By "complementary", is meant that the modifying compound and the PNP become chemically bound by the reactive interaction of the respective reactable groups.

A preferred modifying compound is an amphiphilic compound having ionizable or acid-base reactable groups. Useful amphiphilic compounds have both hydrophobic and hydrophilic groups. The hydrophobic portion of the amphiphilic compound must contain at least 4 carbon atoms, and can be branched, straight chain, aromatic, saturated or unsaturated. Typical hydrophilic portions of the amphiphilic compound include polyoxyethylene, polyoxypropylene, polyacrylamide, or polyvinyl alcohol. The weight average molecular weight, Mw of the amphiphilic compound is less than about 10,000. Useful amphiphilic compounds include quaternary ammonium salts, such as for example, quaternary salt of Ethomeen™ 0/25, supplied by Akzo Nobel Chemical Company, Chicago, Ill. This salt is a quaternary polyethoxylated ammonium salt with the formula $C_{18}H_{35}(CH_3)N(CH_2CH_2O)_xH(CH_2CH_2O)_yH(I)$ where x+y=15 and a molecular weight of about 942. The quaternary salt contains a positively charged nitrogen group which can form a complementary pair with a PNP containing an anionic group, such as for example, a carboxylate group. Triton™ RW-150 supplied by Union Carbide Company, Danbury, Conn. with the formula $t\text{-}C_{12\text{-}14}NH(CH_2CH_2O)_{15}H$ is a polyethoxylated amine which is another useful amphiphilic compound. A preferred amphiphilic compound is a tertiary polyethoxylated amine with the formula $C_{18}H_{37}N(CH_2CH_2O)_xH(CH_2CH_2O)_yH$(where x+y=15) and a molecular weight of about 929 (Ethomeen™ 18/25). The amine base is the second reactable group which is combined and reacted with a PNP containing an acid as the first reactable group.

A preferred covalently bonded pair of complementary reactable groups is JEFFAMINE™ ED-600 (supplied by the Texaco Chemical Company, Houston, Tex.) modifying compound reacted with an acetoacetate-group containing PNP. JEFFAMINE™ ED-600 is a polyether diamine based on a predominately polyethylene oxide backbone. The amine (JEFFAMINE™ ED-600) is the second reactable group which is reacted with a PNP containing acetoacetate as the first reactable group.

A stoichiometric excess of the first complementary reactable group is desirably present relative to the second complementary group in the co-reactive stabilizer. In this aspect of the invention the weight of co-reactive stabilizer for which a stoichiometric equivalent of complementary reactable group is present in the PNPs preferably comprises equal to or greater than 1% by weight based on the total weight of polymer, of the PNP composition. A stoichiometric excess of the co-reactive stabilizer containing the second reactable group may be present relative to the first reactable group. The coreactive stabilizer containing the second reactable group is present in the coating formulation at the level of from 0.005 to 10 molar equivalents, based on the combined molar equivalents of the first reactable group in the PNP and other polymer(s) in the paint formulation. More preferably, the modifying compound is present at the level of from 0.1 to 1.0 molar equivalent.

Post-functionalization of the PNP alternatively is effected before, during, or after the PNP is incorporated into the aqueous composition of the invention. In another embodiment the incorporation of hydrophilic moieties such as starches, sugars, hydroxyethylcellulose, other cellulosics, poly-vinyl alcohols, poly-alkylene oxides, and other colloidal stabilizers into the PNP is effected by grafting onto the PNPs if present during all or part of the free radical polymerization portion of the PNP synthesis. When used, these materials preferably are incorporated in an amount that is at least 1% by weight based on the total weight of PNPs.

In some embodiments the effectiveness of the PNPs in extending open-time is enhanced by the presence of hydrophobic structures incorporated into the PNPs. One route to the incorporation of hydrophobic structures in the PNPs is the inclusion of at least one hydrophobic third monomer in the free radical polymerization portion of the PNP preparation. Hydrophobic ethylenically unsaturated third monomers are those with solubility of less than 5% by weight, preferably less than 2% by weight, most preferably less than 1% by weight, in water at 25° C. This group includes, but is not limited to, alkyl (meth)acrylate monomers, vinylaromatic monomers such as styrene, fluorocarbon monomers, silicon functional monomers, vinyl versatates, vinyl acetates, conjugated dienes, and the like. This hydrophobic monomer is included in an amount of from 0% to 90%, preferably from 10% to 80%, most preferably from 20% to 70%, by weight based on the total weight of the PNPs.

Particularly in the embodiment of the invention in which longer open time, as defined hereinabove, is desired, PNPs and the second polymeric particles are included in the aqueous composition at a level of from 0.1% to 99.9% by weight PNPs based on the total weight of the polymer particles in the aqueous composition. When PNPs are used at a level of from 0.1% to 30% by weight, based on the total weight of the polymer particles, the PNPs typically have a Tg in the range of from −60° C. to 150° C., preferably from 0° C. to 150° C., and most preferably from 35° C. to 150° C. When the PNPs are used at a level of from greater than 30% to 99.9% by weight, based on the total weight of the polymer particles, the PNPs typically have a Tg in the range of from −60° C. to 100° C., preferably from −20° C. to 80° C., and most preferably from −10° C. to 50° C.

PNPs also increase the open time of paint when second polymer particles of larger >50 nm are used in the aqueous composition, and the PNPs are present in the reaction vessel during the production of the larger particles being formed by a second polymerization. This second polymerization is preferably an emulsion polymerization. Without being bound by a particular theory it is believed that the PNPs function as stabilizers (i.e., dispersants) in emulsion polymerizations according to the methods known for using "high acid" polymeric stabilizers (often referred to as "resin supported emulsion polymerization", as disclosed in U.S. Pat. Nos. 4,845,149 and 6,020,061). It is preferred that, in the case of forming a dispersion of larger polymeric particles by a second, preferably emulsion, polymerization in the presence of PNPs, the total level of copolymerized water soluble monomer in the resultant polymer dispersion is from 0.5% to 30%, preferably from 0.75% to 20%, most preferably from 1% to 10%, by weight, based on the total combined weight of PNP and second polymer. The stabilizing moieties include any combination of water soluble monomer(s) and/or modifying compound(s) containing complementary reactable groups, as described previously. The stabilizing moieties in various embodiments are distributed between the PNPs and the second polymer. The distribution of stabilizing moieties may range from 0% to 95% by weight of the stabilizing moieties, based on the total weight of the stabilizing moieties, in the second polymer, and from 5% to 100% of the stabilizing moieties, based on the total weight of the stabilizing moieties, in the PNPs. When the PNPs that are present during the formation of a dispersion of larger polymeric particles by a second, preferably emulsion, polymerization contain acid functionality it is preferable that the acid functionalities of the PNPs are neutralized with a suitable neutralizing base, such as hydroxides (e.g., sodium hydroxide, potassium hydroxide), amines, and preferably ammonia. More preferably, such PNPs are prepared in an aqueous-compatible solvent, neutralized with a base, and diluted in water prior to carrying out the emulsion polymerization. Even more preferably, the aqueous-compatible solvent is at least partially removed, and most preferably substantially completely removed, from the PNP dispersion when it is used to stabilize emulsion polymerizations. In certain cases, other stabilizers, such as surfactants, are present in the dispersion as well. These other stabilizers are present during the formation of the PNP and/or during the second polymerization. Alternatively, all or some of these other stabilizers are also added to the dispersion after completion of the second polymerization.

Among suitable emulsion polymer compositions, any emulsion polymer, copolymer, multi-stage copolymer, interpolymer, core-shell polymer, and the like are capable of being stabilized using the PNPs of the present invention. Although any ethylenically unsaturated monomer is utilizable, it is preferred that the emulsion polymers which are stabilized are prepared from at least one of (meth)acrylic ester and vinylaromatic monomers. In carrying out emulsion polymerizations containing the PNPs of the present invention, all of the typical emulsion polymerization components, conditions, and processes are utilizable, if desired, such as, for example, emulsifiers, initiators, temperatures, chain transfer agents, reactor types, and the like.

In another embodiment of the present invention an aqueous composition including an aqueous dispersion of at least one pigment and PNPs having a mean diameter of 1 to 50 nm, the nanoparticles including, as polymerized units, at least one multi-ethylenically-unsaturated monomer and at least one ethylenically unsaturated water soluble monomer is provided. Such aqueous compositions include aqueous coating compositions and aqueous pigment dispersions. Aqueous coating compositions typically further include an aqueous dispersion of second polymeric particles having a mean diameter of greater than 50 nm. Such aqueous compositions provide greater stability, i.e., storage stability at ambient and higher temperatures, by which is meant herein stability as evidenced by, for example, at least one of: viscosity stability and substantial fredom from flocculation relative to corresponding aqueous coating compositions in which the PNPs are replaced by the same weight of polymeric particles of the same composition having a mean diameter of greater than 50 nm.

The stability in a typical aqueous composition including a pigment is largely a result of complex chemical and physical interactions taking place at the latex and pigment surfaces. Acid containing PNPs provide a much more effective means for dispersing pigments and provide aqueous compositions with greater stability than current technology based mostly on solution polymer dispersants and small particle inorganics such as potassium tripolyphosphate. Without being bound by a particular theory, it is believed that the solution polymer dispersants do not adsorb strongly enough and/or do not provide adequate protection when adsorbed onto pigments. PNPs, being particulate in nature, both adsorb strongly and provide adequate surface protection to prevent flocculation. PNPs have been demonstrated to be effective dispersants for pigments such as $TiO_2$ and mineral extenders. PNPs produce improved rheology (i.e., substantially Newtonian viscosity) at high solids and high PVC compared to prior art dispersants, with good compatibility with emulsion polymers and good storage stability.

As used herein "pigment" includes organic and inorganic particulate water-insoluble non-film-forming compositions. Organic pigments include, for example, phtalocyanine green and voided latex particles as are described in U.S. Pat. No. 4,427,836. Inorganic pigments include titanium dioxide, zinc oxide, red iron oxide, and the like, as well as pigments commonly known as extender pigments such as calcium carbonate, silica, and the like.

PNPs suitable for use in embodiments wherein aqueous composition stability is sought include a copolymerized water soluble monomer, preferably from 5% to 90% by weight, based on PNP weight, acid monomer such as (meth)acrylic acid, itaconic acid, phosphoethyl methacrylate, crotonic acid, maleic anhydride, sulfates, or water soluble nonionic monomer such as ethoxylates where the EO chain length ranges from 1 to 100 and is copolymerizable through a double bond such as provided by a (meth)acrylate, allyl, vinyl, grouping, for example. PNPs in this embodiment are added at from 0.001% to 50.0%, preferably from 0.005% to 10.0%, and most preferably from 0.01 to 5.0% PNP by weight, based on pigment weight.

Pigment prepaints, such as are disclosed in U.S. patent application Ser. No. 2002/0013401, intended for use in the manufacture of paints, exhibit greater stability as defined hereinabove, when incorporating the PNPs of the present invention. Particularly desirable is the ability to provide fluid stable pigment dispersions at high PVC, such as greater than 70% PVC.

In another embodiment of the present invention an aqueous composition including a pigment, an aqueous dispersion of PNPs having a mean diameter of from 1 to 50 nm, the particles including amine functionality and further including, as polymerized units, at least one multi-ethylenically-unsaturated monomer; an anionically-stabilized emulsion polymer having a mean diameter of greater than 50 nm; and a volatile base in an amount sufficient to deprotonate the amine is provided. The aqueous compositions include aqueous coating compositions such as quick-set coatings as exemplified by traffic paint, Exterior Insulation and Finish Systems (EIFS), roof mastics, etc. Such aqueous compositions provide a stable aqueous composition having shorter set-time than the corresponding composition in which the PNPs are replaced by the same weight of a water-soluble polyamine polymer as is taught in U.S. Pat. No. 5,804,627. The greater the amount of water-soluble polyamine polymer that is used, the quicker the system will set. However, there are limitations as to how much water soluble polymer can be added to the emulsion polymer before stability problems such as coagulation, syneresis, solids gradient formation, and sedimentation occur. One solution to this problem is to lower the solids of the prior art composition, but this is not practical because paint formulators need high solids traffic paint formulations to achieve quick setting coatings. PNPs containing amine groups in place of water-soluble polyamine polymers solve this problem.

Preferred PNP compositions include, as copolymerized units, 99 dimethyaminoethyl methacrylate (DMAEMA), 89 DMAEMA/10 methacrylic acid, 99 oxazolidinylethyl methacrylate (OXEMA); all numerical values in weight % based on weight of the PNPs. Amine functional-PNPs are alternatively provided by the following routes: (1) polymerization of monomers which generate amines by hydrolysis, (2) reaction of aziridines with carboxyl-containing polymers, (3) reaction of polymers containing enolic carbonyl group, e.g. acetoacetylethyl methacrylate, with diamines, (4) reaction of amines with epoxy containing polymers, and (5) reaction of amine with polymers containing vinyl benzyl chloride.

The amount of PNPs in the aqueous composition that is sufficient to reduce the setting time of the coating is typically an amount between 20% and 500%, preferably between 50% and 250%, and more preferably between 75% and 150% based on the equivalents of amine functionality per equivalents of anionic charge in the composition.

In another embodiment of the present invention an aqueous composition including a pigment and an aqueous dispersion of PNPs having a mean diameter of 1 to 50 nm, the particles including, as polymerized units, at least one multi-ethylenically-unsaturated monomer and at least 2% by weight, based on polymer particle weight, of at least one ionic ethylenically unsaturated monomer is provided. Preferred is the incorporation of at least 5%, more preferably at least 7% by weight, based on polymer particle weight, of at least one ionic ethylenically unsaturated monomer. Such compositions exhibit improved freeze/thaw stability relative to that of a corresponding aqueous coating compositions in which the PNPs are replaced by the same weight of polymeric particles of the same composition having a mean diameter of greater than 50 nm.

It is desirable to store aqueous coating and aqueous colorant compositions at ambient temperatures. Consequently there is a need for such aqueous compositions to resist deterioration associated in particular with freezing and thawing. Preferably a paint or colorant should remain stable and usable after at least one freeze/thaw cycle. More preferably a paint or colorant should remain usable after at least five freeze/thaw cycles. A method of measuring freeze/thaw resistance is described in ASTM D-2243-82.

Most commonly a water miscible solvent such as ethylene glycol or propylene glycol is used as a freeze/thaw additive in amounts of from 1% to 20% by weight, based on the weight of the aqueous phase. However, such solvents contribute to the total volatile organic content (VOC) of coatings and colorants; it is increasingly desirable to reduce VOCs to the lowest levels possible. Alternative non volatile freeze thaw additives and aids include soluble sugars such as cyclodextrin and glucose, polyols such as glycerol, polyethers such as polyethylene glycol, gums, starches and proteins. However these too have certain disadvantages. Most seriously, they are all water soluble and contribute to the water sensitivity of a resultant coating. It has now been found that many of the aforementioned problems are overcome by including the PNPs of the present invention in aqueous compositions such as colorant dispersions, inks, coatings and paints.

The PNPs of this embodiment contain at least 2.0% by wt., based on PNP weight, of a copolymerized ionic ethylenically unsaturated monomer. Preferred incorporated ionic groups are carboxylate, sulfonate, and their ammonium, sodium, potassium and lithium salts. The composition of the PNP preferably contains a combination of both hydrophilic nonionic groups such as —OH and —$CH_2CH_2O$— and long chain alkyl methacrylates such as lauryl methacrylate, stearyl methacrylate or behenyl methacrylate. Preferred third monomers include 2-hydroxyethyl methacrylate, 2-hydroxypropyl methacrylate, and polyethylene glycol methacrylate monomers such as $HO(CH_2CH_2O)_3$-methacrylate. The PNPs of this embodiment have an acid value of from 0 to 250 (mg KOH/g PNP solids), more preferably from 1 to 150 and still more preferably from 2 to about 100, an amine value of from 0 to 150, and an hydroxyl number of about 0 to 250 (mg KOH/g PNP solids).

Typically, the amount of PNPs required to sufficiently stabilize a colorant or paint for freeze/thaw resistance is from 0.1% to 10%, preferably 0.1% to 5% by weight, based on the weight of paint or colorant solids.

Test Methods Used in the Examples:

Open Time Test Method

Open time is defined as the length of time a coating remains wet enough to make repairs. The test is performed at a controlled temperature of 25° C. and controlled relative humidity of 50% with no airflow across the chart. A Black Leneta Chart was secured to an Aluminum Drawdown Plate. The test coating composition was drawn down lengthwise on the chart using a 5 mil drawdown block. A stopwatch was started immediately and 2 parallel lines were made down the length of the film with a wooden stick. At one minute time intervals, a 1" Nylon Brush was wet with ½" to ¾" of the test paint (about 2 g). The drawdown was immediately brushed across from left to right trying to cover the lines with the fresh paint; 20 strokes with about 100 g of force on the brush were used. The last direction was repeated for eight minutes. For paints with longer open times, all steps were repeated and 8 minutes was allowed to lapse before brushing was started again. The test substrate was allowed to dry for 16–24 hours at the controlled temperature and humidity. The chart was examined for defects and the latest time interval at which the lines that were made down the length of the drawdown could no longer be seen was reported (time prior to when the marks first show through).

Viscosity Test Methods

ICI viscosity was measured according to ASTM D3205-77 using an ICI Cone and Plate Viscometer thermostatically controlled to operate at 25° C., with 0 to 10-P (0 to 1 Pa s) or 0 to 5-P cone producing a rate of shear of 10,000 s$^{-1}$. KU viscosity was measured according to ASTM D562-81 (Reapproved 1985) using a Stormer Viscometer; Brookfield KU-1.

EXAMPLE 1

Preparation of an Aqueous Dispersion of PNPs

A dispersion of methyl methacrylate(MMA)/methacrylic acid(MAA)/trimethylol propane triacrylate(TMPTA) (70/20/10 wt. %) PNPs was prepared via solution polymerization in isopropyl alcohol (IPA) as follows: A 5 liter reactor was fitted with a thermocouple, a temperature controller, a purge gas inlet, a water-cooled reflux condenser with purge gas outlet, a stirrer, and a monomer feed line. To a separate vessel was charged 450 grams of a monomer mixture (A) containing 315 g MMA, 90 g MAA, and 45 g TMPTA. To an additional vessel was charged an initiator mix (B) consisting of 18 g of a 75% solution of t-amyl peroxypivalate in mineral spirits (Triganox 125-C75), and 113 g IPA. A charge of 2330 g IPA was added to the reactor. After sweeping the reactor with nitrogen for approximately 30 minutes, heat was applied to bring the reactor charge to 79° C. When the contents of the reactor reached 79° C., a dual feed of both the monomer mixture (A) and the initiator mix (B) to the reactor. The two mixtures were fed uniformly using feed pumps over 120 minutes. At the end of the monomer and initiator feeds, the batch was held at 79° C. for 30 minutes before adding the three initiator solutions consisting of 9 g of a 75% solution of t-amyl peroxypivalate in mineral spirits (TRIGANOX™ 125-C75), and 22.5 g IPA. Additional initiator was added. The batch was then held at 79° C. for an additional 2½ hours. At the end of the final hold, the polymerized MAA units of the PNPs were neutralized by addition to the PNP dispersion of a mixture of 42.5 g of an aqueous 50% solution of $NH_4OH$ and 450 g water. The neutralized PNP dispersion was transferred to a roto-evaporator and stripped of solvent at 35° C. under vacuum. After removing substantially all of the solvent, the PNP dispersion was further diluted with water to 40 wt. % PNP in water. Particle size was measured at 5.0 nm.

EXAMPLE 2

Preparation of Aqueous Dispersion of PNPs

PNPs of butyl acrylate/methyl methacrylate/acrylic acid/allyl methacrylate (49.5/33/7.5/10 wt. %) were prepared via solution polymerization. A 1 liter reactor was fitted with a thermocouple, a temperature controller, a purge gas inlet, a water-cooled reflux condenser with purge gas outlet, a stirrer, and a monomer feed line. To a separate vessel was charged 150 g of a monomer mixture (A) consisting of 74.3 g butyl acrylate (BA), 49.5 g methyl methacrylate (MMA), 11.3 g acrylic acid (AA), and 15.0 g allyl methacrylate (ALMA). To an additional vessel was charged an initiator mix (B) consisting of 3.0 g of a 75% solution of t-amyl peroxypivalate in mineral spirits (Triganox 125-C75), and 37.5 g methyl ethyl ketone (MEK). A charge of 528 g MEK was added to the reactor. After sweeping the reactor with nitrogen for approximately 30 minutes, heat was applied to bring the reactor charge to 78° C. When the contents of the reactor reached 78° C., a dual feed of both the monomer mixture (A) and the initiator mix (B) was provided to the reactor. The two mixtures were fed uniformly using feed pumps over 120 minutes. At the end of the monomer and initiator feeds, the batch was held at 78° C. for 30 minutes before adding additional initiator. The batch was then held at 78° C. for an additional 2½ hours.

Then the batch was neutralized with a mixture of 11.0 g of a 50% aqueous solution of $NH_4OH$ and 150 g water. The neutralized polymer solution was transferred to a roto-evaporator and stripped of solvent at 45° C. under vacuum.

After removing all solvent the batch was further diluted with water to ~30% by weight polymer in water and pH adjusted to 8.0. Particle size was measured at ~4.7 nm.

EXAMPLE 3

Preparation of Aqueous Dispersion of PNPs

PNPs of methyl methacrylate/acrylic acid/trimethylol propane triacrylate (75/20/5 wt. %) was prepared via solution polymerization at 20% solids in IPA as described in Example 1. Particle size was measured at 2.4 nm.

At the end of the final hold, a portion of the batch was charged to a 5 fold excess of heptane. The nanoparticle readily precipitated from the heptane solution, was filtered using a Buchner filter, and dried in a vacuum oven at 60° C. under vacuum to remove all volatile material. To 100 g dried PNPs was added 300 g water and 20.5 g of a 50% aqueous NH$_4$OH solution. The mixture was agitated for 1 hour to achieve a clear homogeneous solution. Particle size was measured at 2.3 nm.

EXAMPLE 4

Preparation of Aqueous Dispersion of PNPs

Following the process of Example 3, at the end of the final hold, 100 g of the PNP dispersion was neutralized with 4.4 gm of a 50% aqueous solution of NaOH. The neutralized PNP dispersion was charged to a five-fold excess of heptane to precipitate the PNPs. The precipitated PNPs were isolated by filtration and dried to constant weight in a vacuum oven at ~60° C. The dried PNPs were then re-dispersed into water to provide a 30% solids solution. Particle size was 2.4 nm.

EXAMPLE 5

Preparation of Aqueous Dispersion of PNPs

PNPs of butyl acrylate/methyl methacrylate/acrylic acid/ trimethyol propane triacrylate (35/35/20/10 wt. %) were prepared via solution polymerization. A 5-liter reactor was fitted with a thermocouple, a temperature controller, a purge gas inlet, a water-cooled reflux condenser with purge gas outlet, a stirrer, and a monomer feed line. To a separate vessel was charged 480 g of a monomer mixture (A) consisting of 168.0 g butyl acrylate (BA), 168.0 g methyl methacrylate (MMA), 96.0 g acrylic acid (AA), 48.0 g trimethyol propane triacrylate (TMPTA and ), 19.2 grams of a 75% solution of t-amyl peroxypivalate in mineral spirits (Triganox 125-C75) and 120.0 grams of isopropanol (IPrOH). A charge of 2,480.0 grams of IPrOH was added to the reactor. After sweeping the reactor with nitrogen for approximately 30 minutes, heat was applied to bring the reactor charge to 79° C. When the contents of the reactor reached 79° C., a feed of the monomer mixture was added to the reactor uniformly over 120 minutes using feed pumps. At the end of the monomer feed, the batch was held at 79° C. for 30 minutes before adding additional initiator. The batch was then held at 79° C. for an additional 2½ hours. At the end of the final hold, the batch was neutralized with a mixture of 80.9 g of a 28% aqueous solution of NH$_4$OH diluted in 480.0 grams of water. The neutralized polymer solution was transferred to a roto-evaporator and stripped of solvent at 65° C. under vacuum. After removing the solvent the batch was further diluted with additional water to 34.7% polymer in water and final pH was adjusted to 9.0. Particle size was measured at 4.0 nm.

EXAMPLE 6

Preparation of Aqueous Dispersion of PNP

PNPs of butyl acrylate/methyl methacrylate/acrylic acid/ acetoacetoxy ethylmethacrylate/trimethylol propane triacrylate (30/30/20/10/10 wt. %) were prepared via solution polymerization by the method described in Example 5 except that after removing the solvent the batch was further diluted with additional water to 49.5% polymer in water and final pH was adjusted to 9.0. Particle size was measured at 4.0 nm.

EXAMPLE 7

Preparation of Aqueous Dispersion of Post-functionalized PNPs

PNPs of butyl acrylate/methyl methacrylate/acrylic acid/ acetoacetoxy ethylmethacrylate/trimethylol propane triacrylate (30/30/20/10/10 wt. %) are prepared via solution polymerization by the method described in Example 5 except that after the 2½ hour final hold 67.2 grams JEFFAMINE™ ED-600 is added to the reactor and the reactor contents are allowed to mix for 1 hour prior to the addition of a mixture of 80.9 g 28% aqueous solution of NH$_4$OH diluted in 480.0 g water.

EXAMPLE 8

Preparation of Aqueous Dispersion of PNPs

PNPs of butyl acrylate/methyl methacrylate/acrylic acid/ BISOMER™ S10W/trimethylol propane triacrylate (30/30/ 10/20/10 wt. %) are prepared by the method of Example 5. (Bisomer is a trade mark of the British Petroleum Company plc and is used by INSPEC UK under license. Bisomer Monomers supplied by INSPEC UK).

EXAMPLE 9

Preparation of Emulsion Polymer Made in the Presence of PNPs

A 2-liter reactor was fitted with a thermocouple, a temperature controller, a purge gas inlet, a water-cooled reflux condenser with purge gas outlet, a stirrer, and a monomer feed line and catalyst feed line. To a separate vessel was charged 310.8 g monomer mixture (A) consisting of 155.4 g butyl acrylate (BA) and 155.4 g methyl methacrylate (MMA).). A charge of 157.3 g deionized water and 298.5 g of the PNPs described in Example 5 was added to the reactor. After sweeping the reactor with nitrogen for 30 minutes, heat was applied. When the contents of the reactor reached 85° C., 6.8 grams of monomer from mixture A was added to the reactor along with 0.33 g ammonium persulfate (APS) dissolved in 3.0 g water. After 15 minutes an additional 1.0 g APS dissolved in 17.8 g water and 0.1 g 28% ammonia was added to the reactor. The remainder of monomer mixture A was then fed to the reactor uniformly over 140 minutes thru the monomer feed line using feed pumps. Sixty minutes into the monomer feed a separate feed consisting of 1.2 g APS dissolved in 29.9 g water and 0.12 g 28% ammonia was fed uniformly thru a catalyst feed line with a catalyst feed pump. When the feed was finished the reactor was heated to 87° C. and held for 60 minutes then cooled to room temperature and filtered thru US standard sieves 100 and 325 mesh. The resulting emulsion polymer had the following properties: 50.5 weight % solids, pH 8.1, Brookfield Viscosity 2,150 cps, particle size 134 nm.

EXAMPLE 10

Preparation of Emulsion Polymer in the Presence of PNPs

A 2-liter reactor was fitted with a thermocouple, a temperature controller, a purge gas inlet, a water-cooled reflux condenser with purge gas outlet, a stirrer, and a monomer feed line and catalyst feed line. To a separate vessel was charged 310.8 g of monomer mixture (A) consisting of 155.4 g butyl acrylate (BA) and 155.4 g methyl methacrylate (MMA).). A charge of 246.6 g deionized water and 209.3 g of the PNP described in Example 6 was added to the reactor. After sweeping the reactor with nitrogen for approximately 30 minutes, heat was applied to the reactor. When the contents of the reactor reached 85° C., 6.8 g of monomer from mixture A was added to the the reactor along with 0.33 g ammonium persulfate (APS) dissolved in 3.0 g water. After 15 minutes an additional 1.0 g APS dissolved in 17.8 g water and 0.1 g 28% ammonia was added to the reactor. The remainder of monomer mixture A was then fed to the reactor uniformly over 140 minutes thru the monomer feed line using feed pumps. Sixty minutes into the monomer feed a separate feed of 1.2 g APS dissolved in 29.9 g water and 0.12 g 28% ammonia is fed uniformly thru a catalyst feed line with a catalyst feed pump. One hundred and five minutes into monomer feed A 25 g water was added to the reactor. One hundred thirty minutes into monomer feed A another 25 g water was added to the reactor. When the catalyst feed was finished the reactor was heated to 87° C. and held for 60 minutes then cooled to room temperature and filtered thru US standard sieves 100 and 325 mesh. The resulting emulsion polymer had the following properties: 47.8 weight % solids, pH 8.1, Brookfield Viscosity 7,000 cps, particle size 131 nm.

EXAMPLE 11–12

Preparation of Aqueous Coating Compositions Including PNP

This example demonstrates the formation of an aqueous coating composition from the emulsion polymers prepared in the presence of PNPs of Examples 9–10.

| Material | Example 11 | Example 12 |
|---|---|---|
| Grind: | | |
| Water | 50.0 | 50.0 |
| TAMOL ™ 731A | 11.4 | 11.4 |
| Tego FOAMEX ™ 810 | 1.0 | 1.0 |
| SURFYNOL ™ CT-111 | 2.0 | 2.0 |
| TI-PURE ™ R-706 | 228.4 | 228.4 |
| Letdown: | | |
| Emulsion of Example 9 | 281 (solids) | |
| Emulsion of Example 10 | | 281 (solids) |
| Water | 406 | 406 |
| TEXANOL ™ | 16.7 | 16.7 |
| SURFYNOL ™ CT-11 | 1.0 | 1.0 |
| ACRYSOL ™ RM-2020 NPR | 24 | 24 |
| ACRYSOL ™ RM-8W | 21 | 21 |

TAMOL and ACRYSOL are trademarks of Rohm and Haas Company, Philadelphia, PA;
FOAMEX is a trademark of Degussa-Huls Corp., Ridgefield Park, NJ;
SURFYNOL is a trademark of Air Products and Chemicals Inc., Allentown, PA;
TI-PURE is a trademark of DuPont Company, Wilmington, DE;
TEXANOL is a trademark of Eastman Chemical Company, Kingsport, TN;

COMPARATIVE EXAMPLE A

Preparation of Aqueous Coating Compositions

Aqueous coating compositions were made using an anionic emulsion polymer having a mean particle diameter of 100 nm in the same weight ratio as for Examples 11–12.

| Material | Comp. A |
|---|---|
| Grind: | |
| Water | 50.0 |
| TAMOL ™ 731A | 11.4 |
| Tego FOAMEX ™ 810 | 1.0 |
| SURFYNOL ™ CT-111 | 2.0 |
| TI-PURE ™ R-706 | 228.4 |
| Letdown: | |
| Emulsion Polymer | 280 (solids) |
| Water | 416 |
| TEXANOL ™ | 19.4 |
| SURFYNOL ™ CT-111 | 1.0 |
| ACRYSOL ™ RM-2020 NPR | 29 |
| ACRYSOL ™ RM-8W | 6 |

EXAMPLE 13

Properties of Aqueous Coating Compositions

TABLE 13.1

| Coating of Ex. No. | Initial Viscosity KU/ICI | 24 Hr Viscosity KU/ICI | Open Time (in min) |
|---|---|---|---|
| 12 | 97/1.15 | 100/1.2 | 3 |
| 11 | 98/1.3 | 96/1.2 | 5 |
| Comp. A | 99/1.2 | 99/1.2 | <1 |

Aqueous coating compositions including PNPs of Examples 11–12 of this invention exhibited open time superior to that of Comparative Example A.

EXAMPLE 14–15

Formation of an Aqueous Composition Including PNPs and a Anionic Emulsion Binder

| Material | Example 14 (in g) | Example 15 (in g) |
|---|---|---|
| Grind: | | |
| Water | 50.0 | 50.0 |
| TAMOL ™ 731A | 11.4 | 11.4 |
| Tego FOAMEX 810 | 1.0 | 1.0 |
| SURFYNOL ™ CT-111 | 2.0 | 2.0 |
| TI PURE ™ R-706 | 228.4 | 228.4 |
| Letdown: | | |
| Anionic emulsion polymer (mean diameter 100 nm) | 259 (solids) | 259 (solids) |
| PNPs of Example 5 | 21 (solids) | |
| PNPs of Example 5 | | 21 (solids) |
| Water | 416 | 416 |
| TEXANOL ™ | 19.4 | 19.4 |
| SURFYNOL ™ CT-111 | 1.0 | 1.0 |
| ACRYSOL ™ RM-2020 NPR | 29 | 29 |
| ACRYSOL ™ RM-8W | 6 | 6 |

EXAMPLES 16–21

Preparation and Evaluation of Aqueous Compositions

Aqueous coating compositions including PNPs and an anionic emulsion polymer are prepared and evaluated as presented in Tables 16.1 and 16.2

TABLE 16.1

| Material | \multicolumn{6}{c}{Aqueous coating compositions} |
|---|---|---|---|---|---|---|
| | 16 | 17 | 18 | 19 | 20 | 21 |
| Grind: | | | | | | |
| Water | 50.0 | 50.0 | 50.0 | 50.0 | 50.0 | 50.0 |
| TAMOL ™ 731A | 11.4 | 11.4 | | | | |
| PNPs of Example 5 | | | 3.7 (solids) | | 3.7 (solids) | |
| PNPs of Example 6 | | | | 5.5 (solids) | | 5.5 (solids) |
| Tego FOAMEX ™ 810 | 1.0 | 1.0 | 1.0 | 1.0 | 1.0 | 1.0 |
| SURFYNOL ™ CT-111 | 2.0 | 2.0 | 2.0 | 2.0 | 2.0 | 2.0 |
| TI-PURE ™ R-706 | 228.4 | 228.4 | 228.4 | 228.4 | 228.4 | 228.4 |
| Letdown: | | | | | | |
| Anionic Emulsion Polymer (100 nm) | 259 (solids) | 259 (solids) | 280 (solids) | 280 (solids) | 259 (solids) | 259 (solids) |
| PNPs of Example 5 | 21 (solids) | | | | 21 (solids) | |
| PNPs of Example 6 | | 21 (solids) | | | | 21 (solids) |
| Water | 416 | 416 | 416 | 416 | 416 | 416 |
| TEXANOL ™ | 19.4 | 19.4 | 19.4 | 19.4 | 19.4 | 19.4 |
| SURFYNOL ™ CT-111 | 1.0 | 1.0 | 1.0 | 1.0 | 1.0 | 1.0 |
| ACRYSOL ™ RM-2020 NPR | 29 | 29 | 29 | 29 | 29 | 29 |
| ACRYSOL ™ RM-8W | 6 | 6 | 6 | 6 | 6 | 6 |

TABLE 16.2

Properties of Aqueous Coating Compositions

| Coating Ex. No. | Description | Initial Viscosity KU/ICI | 24 Hr Viscosity KU/ICI |
|---|---|---|---|
| Comp A | Comparative | 99/1.2 | 99/1.2 |
| 16 | Blend | 100/1.2 | 102/1.2 |
| 17 | Blend | 101/1.15 | 104/1.2 |
| 18 | Disp | 99/1.2 | 98/1.2 |
| 19 | Disp | 101/1.2 | 99/1.2 |
| 20 | Blend + Disp | 104/1.1 | 105/1.1 |
| 21 | Blend + Disp | 99/1.2 | 101/1.2 |

The aqueous coating compositions Examples 16–21 of this invention exhibit good stability and longer open time relative to that of Comparative Example A.

EXAMPLES 22–26

Preparation and Evaluation of Aqueous Coating Compositions

Aqueous coating compositions are prepared as in Examples 14–15 except for the PNPs used which are presented in Table 22.1

Table 22.1. Aqueous coating compositions

| Coating Ex. No. | PNP Blend Vehicle |
|---|---|
| 22 | Example 1 |
| 23 | Example 2 |
| 24 | Example 3 |
| 25 | Example 4 |
| 26 | Example 7 |

The aqueous coating compositions Examples 22–26 of this invention exhibit good stability and longer open time relative to that of Comparative Example A.

EXAMPLES 27–37

Preparation of Emulsion Polymers in the Presence of PNPs

The PNPs listed in the following table are prepared and are used in emulsion polymerizations according to Example 9. Utilizing PNPs of different compositions results in different particle sized latexes and variations on the improved properties they exhibit. The resulting emulsion polymers are used for preparing aqueous coating compositions.

TABLE 27.1

| Compositions of PNPs | | |
|---|---|---|
| Example | Composition | Particle Size (nm) |
| 27 | 70 MMA/20 MAA/10 TMPTA | 10 |
| 28 | 80 MMA/10 AA/10 TMPTA | 10 |
| 29 | 75 MMA/20 AA/5 ALMA | 8 |
| 30 | 35 MMA/35 BA/20 AA/10 TMPTA | 8 |
| 31 | 30 MMA/30 BA/30 AA/10 TMPTA | 10 |
| 32 | 60 BA/30 AA/10 TMPTA | 10 |
| 33 | 20 MMA/40 2-EHA/30 AA/10 TMPTA | 10 |
| 34 | 30 Sty/30 MMA/20 AA/10 TMPTA/10 AAEM | 10 |
| 35 | 70 MMA/20 PEM/10 TMPTA | 15 |
| 36 | 20 BA/60 AA/20 TMPTA | 15 |
| 37 | 80 AA/20 TMPTA | 20 |

EXAMPLE 38

Preparation and Evaluation of Aqueous Compositions

A white semigloss latex paint is formulated with 35% volume solids (VS), 20% pigment volume concentration (PVC) TiO$_2$ plus 1% PVC Zinc Oxide. The emulsion polymer is RHOPLEX™ AC-264 and the thickener a combination of CELLOSIZE™ QP-3300 and ACRYSOL™ RM-2020NPR to a viscosity of 92 Krebs units. (CELLOSIZE is a trademark of Hercules Inc., Wilmington, Del.) Additional ingredients such as defoamers, biocides, mildewcides, wet edge solvents, surfactants, coalescent, tint aids, water etc are used as is customary to one skilled in the art. In one version of this composition the pigment is dispersed with 3% TAMOL™ 165A on total pigment solids. The paint is equilibrated for 24 hours. A sample of the paint is spread on a test card with a 3 mil Bird applicator and dried at 25° C. and 50% RH for 24 hours. The gloss is measured at 60° and found to be 28%. The paint is stored at 50° C. for 30 days, allowed to equilibrate to room temperature and another sample is cast on a test card. The gloss is found to be 16%. In another version of this composition the pigment is dispersed instead using 3% PNP. The gloss is now found to be 46%. After heat age testing the gloss is found to be 42%. The higher gloss and improved gloss stability after heat aging indicates reduced flocculation and improved paint stability.

EXAMPLE 39

Preparation of Aqueous Dispersion of PNPs

PNPs of butyl acrylate/methyl methacrylate/phosphoethylmethacrylate/acrylic acid/trimethyol propane triacrylate (36/14/20/20/10 wt. %) were prepared via solution polymerization. A 5-liter reactor was fitted with a thermocouple, a temperature controller, a purge gas inlet, a water-cooled reflux condenser with purge gas outlet, a stirrer, and a monomer feed line. To a separate vessel was charged 480 g of a monomer mixture (A) consisting of 172.8.0 g butyl acrylate (BA), 67.2 g methyl methacrylate (MMA), 96.0 g phosphoethyl methacrylate (PEM), 96.0 g acrylic acid (AA), 48.0 g trimethyol propane triacrylate (TMPTA and), 19.2 grams of a 75% solution of t-amyl peroxypivalate in mineral spirits and 120.0 g IPA. A charge of 2,462.0 g IPA was added to the reactor. After sweeping the reactor with nitrogen for 30 minutes, heat was applied to bring the reactor charge to 79° C. When the contents of the reactor reached 79° C., a feed of the monomer mixture was added to the reactor uniformly over 120 minutes using feed pumps. At the end of the monomer feed, the batch was held at 79° C. for 30 minutes before adding additional initiator. The batch was then held at 79° C. for and additional 2½ hours. At the end of the final hold, the batch was neutralized with a mixture of 80.9 g of a 28% aqueous solution of NH$_4$OH diluted in 261.4 g water. The neutralized polymer solution was transferred to a roto-evaporator and stripped of solvent at 65° C. under full house vacuum. After removing the solvent the batch was further diluted with additional water to 19.8% polymer in water. After rotoevaporation the final pH was 7.2. Particle size was measured at 2.2 nm.

EXAMPLE 40

Improved Aqueous Coating Stability with PNP

A stable water based paint was made using the PNP of Example 39 neutralized with NH4 as a dispersant in the formulation listed in Table 40.1. Properties of the composition are found in Table 40.2

TABLE 40.1

| Aqueous coating composition | |
|---|---|
| Grind: | |
| Water | 95.9 grams |
| Propylene glycol | 30.0 |
| PNP of Example 39 | 19.3 |
| TERGITOL ™ NP-40 | 4.0 |
| COLLOID ™ 643 | 1.5 |
| OPTIWHITE ™ | 50.0 |
| OMYACARB ™ 5 | 60.0 |
| MISTRON ™ 353 | 70.0 |
| TI-PURE ™ R-902 | 200.0 |
| Letdown: | |
| RHOPLEX ™ RES-3083 | 260.0 |
| RHOPLEX ™ SG-10M | 130.0 |
| TEXANOL ™ | 20.8 |
| COLLOID ™ 643 | 1.5 |
| Ammonia (28%) | 3.2 |

TABLE 40.1-continued

| Aqueous coating composition | |
|---|---|
| ACRYSOL ™ DR-73 (15%) | 39.5 |
| Water | 136.8 |

TERGITOL is a trademark of Union Carbide Corporation, Danbury, Conn.; COLLOID is a trademark of Rhodia, Inc., Cranbury, N.J.; OPTIWHITE is a trademark of Burgess Pigment Co., Macon, Ga.; OMYACARB is a trademark of Omya, Inc., Alpharetta, Ga.; MISTRON is a trademark of Luzenac North America, Denver, Colo.

TABLE 40.2

| Aqueous coating composition properties | |
|---|---|
| White untinted coating | |
| Equilibrated KU viscosity | 104 |
| KU after heat age[1] | 111 |
| Equlibrated Brookfield[2] | 8400 cPs |
| Brookfield after heat age | 9100 cPs |
| Opacity stability[3] | |
| Equilibrated | 0.973 |
| After 1 week RT age | 0.966 |
| After heat age | 0.970 |
| 60 Degree Gloss stability[4] | |
| Equilibrated | 5.4 |
| After 1 week RT age | 5.2 |
| After heat age | 5.5 |
| TINTED PROPERTIES: | |
| Color Drift Y reflectance[5] | |
| Blue equilibrated | 41.6 |
| Blue after 1 week RT age | 41.4 |
| Blue after heat age | 41.2 |
| Black equilibrated | 30.2 |
| Black after 1 week RT age | 30.2 |
| Black after heat age | 30.2 |
| Red equilibrated | 29.7 |
| Red after 1 week RT age | 29.6 |
| Red after heat age | 29.6 |
| Rub-up (Delta E)[6] | |
| Blue | 0.58 |
| Black | 0.50 |
| Red | 0.41 |
| 60 Degree Gloss Stability | |
| Blue equilibrated | 3.8 |
| Blue after 1 week RT age | 3.8 |
| Blue after heat age | 4.3 |
| Black equilibrated | 3.9 |
| Black after 1 week RT age | 3.8 |
| Black after heat age | 4.3 |
| Red equilibrated | 3.9 |
| Red after 1 week RT age | 3.7 |
| Red after heat age | 4.1 |

Notes: (1) All heat age measurements carried out after heat aging for 10 days at 60° C., followed by removal from the oven and equilibration to room temperature conditions, and hand shearing of the paint to uniform consistency (2) All Brookfield measurements were carried out on a Brookfield DV-1+ viscometer at 6 RPM using a #4 spindle (3) Opacity was measured using a 3 mil drawdown over a combination black and white Leneta chart. Opacity is the fraction of a black substrate that is hidden by the paint based on Y-reflectance of the paint over a black area of the drawdown chart divided by Y-reflectance of the paint over a white area of the drawdown chart. Drawdowns were prepared for the equilibrated paint, the paint after aging at room temp. on the bench for 1 week, and after aging in the oven for 10 days.

(4) 60 degree gloss was measured using a 3 mil wet drawdown over a white Leneta chart.

(5) Y-reflectance measured using a Colorgard 45 degree/0 degree reflectometer. Paints were tinted using 4 oz tint/gallon of paint, using Colortrend 888 colorants including Phthalo Blue, Lamp Black, and Red Iron Oxide.

(6)Rub-up was determined using the following procedure: A 2 mil wet drawdown was prepared over a Leneta WB chart using a wire wound drawdown rod. The paint was dried for 16 hours at room temperature. A #14 rubber stopper with a 3 mil layer of smooth ping pong rubber on the bottom surface, with the ping-pong rubber covered by a disposable vinyl glove pulled taut across the rubber surface and secured on the sides of the stopper with thumb tacks was used for the next part of the test. A second coat of paint was applied over the first now dry coat, and rubbed up with the stopper device with the vinyl in contact with the wet paint. 25 rub cycles were applied using a firm circular motion. The charts were dried overnight. The delta E values were obtained using a Hunter Ultrascan XE Colorimeter using a 10 degree observer, D65 light source, and L*, a*, b* color coordinates. Note, delta E is a measure of the change in color between the rubbed and unrubbed areas of the drawdown. A delta E of less than 1 is judged to be quite good, meaning the color is well accepted within the paint and little or no flocculation exists.

The aqueous coating composition of Example 40 of the invention was judged to be stable based on the results shown in Table 40.2. Specifically, the KU and Brookfield viscosities did not change significantly when comparing the equilibrated to the heat aged results. In addition, other white paint properties did not indicate any instabilities, as judged by a lack of change in opacity and gloss as a function of time and heat aging. Furthermore, tinted properties also remained stable as a function of time and heat aging, as evidenced by the lack of drift in both the Y-reflectance and 60 degree gloss values as a function of time and heat aging. Finally, the tinted paints did not show any evidence of a significant rub-up problem. If instabilities were present, we would expect at least one and probably several of these properties to indicate a problem. Since all properties look good, we conclude that this formulation resulted in a stable paint.

EXAMPLE 41

Preparation of Aqueous Dispersion of PNP Containing Amine Groups

An Squeous Dispersion of Oxazolidinylethyl Methacrylate/Methacrylic Acid/Trimethylol Propane Tiacrylate (80/10/10 wt. %) PNPs is Prepared According to the Process of Example 1.

EXAMPLE 42

Preparation of Comparative Polyamine and Anionically Stabilized Emulsion Polymer Comparative Polyamine Solution Polymer.

To a 2-liter reactor containing 600 g deionized (DI) water under a nitrogen atmosphere at 60° C., 2.8 g of an aqueous solution of ferrous sulfate heptahydrate (0.15% by weight), 16.2 g glacial acetic acid, and 0.8 g of an aqueous solution of the tetrasodium salt of ethylenediamine tetraacetic acid (1% by weight) diluted with 10 g DI water are added with stirring. A feed composed of 200 g 2-(3-oxazolidinyl)ethyl methacrylate and 100 g DI water is added over a 2 hour period. Simultaneously, feeds composed of 2 g t-butylhydroperoxide (70% active) dissolved in 23 g DI water and 2 g sodium sulfoxylate formaldehyde dihydrate dissolved in 23 g DI water are added over a 2 hour period. After completion of the feeds the reaction is held at 60° C. for 30 minutes then 0.16 g t-butylhydroperoxide (70% active) dissolved in 10 g DI water is added. Fifteen minutes later, 0.1 g t-butylhydroperoxide (70% active) dissolved in 10 g DI water and 0.06 g sodium sulfoxylate formaldehyde dihydrate dissolved in 10 g DI water are added. Fifteen minutes later, the reaction is cooled to room temperature. The final reaction mixture has a pH around 8 after addition of ammonium hydroxide, solids content of approximately 20% and Brookfield viscosity <500 cps.

Anionic Emulsion Polymer Synthesis

To 3583 g DI water under a nitrogen atmosphere at 90° C. are added 67.9 g sodium lauryl sulfate (28% active), 547 g monomer mix (Table 41.1), 33 g sodium carbonate dissolved in 196 g DI water, and 24 g sodium persulfate dissolved in 98 g DI water to form a reaction mixture to which the following monomer mixture is added over 3 hours at 81C along with a solution of 9.7 g sodium persulfate dissolved in 440 g DI water.

TABLE 42.1

| Components of monomer mixture | Weight of component in grams (g) |
| --- | --- |
| DI water | 3959 |
| Sodium lauryl sulfate (28% active) | 67.9 |
| Butyl acrylate | 4332 |
| Methyl methacrylate | 5054 |
| Methacrylic acid | 124 |

At the end of the polymerization, 0.06 g $FeSO_4$ in 40 g DI water, 7.8 g t-butylhydroperoxide in 88 g DI water and 2.9 g sodium sulfoxylate formaldehyde in 176 g DI water are added. Ammonium hydroxide is added to give a final pH=10.3, followed by the addition of 26 g of a 37% formaldehyde solution. The resulting latex polymer has a solids content of 51.7% and an average particle diameter of 172 nm.

EXAMPLE 43

Blends of Latex with PNP and Comparative Polyamine

Emulsion polymer of Example 41 is blended with PNP example 1 and, alternatively, with the polyamine compara-tive of Example 41 at levels listed in Table 2. The blends are heated aged for 10 days at 60C. If a sample shows syneresis it fails stability testing.

TABLE 43.1

Evaluation of stability

| Example | PNP of Example 40 (% solids on emulsion polymer solids) | Polyamine of Example 41 (% solids onemulsion polymer solids | Stability test results |
| --- | --- | --- | --- |
| Comp. B | — | 0.5 | Stable, no syneresis |
| Comp. C | — | 1.5 | 0.5 cm syneresis |
| Comp. D | — | 1.8 | 1.0 cm syneresis |
| 43-1 | 0.5 | — | Stable, no syneresis |
| 43-2 | 1.5 | — | Stable, no syneresis |
| 43-3 | 1.8 | — | Stable, no syneresis |

Aqueous compositions of the invention 43-1, -2, -3 containing PNP exhibit better stability across the range of amine addition relative to those of the comparative polyamine.

EXAMPLE 44

Preparation of Aqueous Traffic Marking Compositions

Latex blend Examples Comp. D and 43-3 are formulated into traffic marking compositions according to the following formulations. The ingredients are added in the order given in Table 44.1 under low shear laboratory mixing. After addition of the OMYACARB™ 5, stirring is continued for 15 minutes before the addition of the remaining ingredients.

TABLE 44.1

Aqueous coating compositions (all quantities in grams)

| Coating No. | 44-1 | 44-2 |
| --- | --- | --- |
| 43-3 composition | 627.7 | — |
| Comp. D composition | — | 627.7 |
| TAMOL ® 901 | 9.8 | 9.8 |
| SURFYNOL ™ CT-136 | 3.8 | 3.8 |
| DREWPLUS ™ L-493 | 2.7 | 2.7 |
| TIPURE ™ R-900 | 136 | 136 |
| OMYACARB ™ -5 | 1035 | 1035 |
| methanol | 40.8 | 40.8 |
| TEXANOL ™ | 31.9 | 31.9 |
| Water | 25.8 | 25.8 |
| DREWPLUS ™ L-493 | 4.8 | 4.8 |

DREWPLUS is a trademark of Ashland Chemical Co., Columbus, OH

TABLE 44.2

Aqueous coating composition test results

| | 44-1 | 44-2 |
| --- | --- | --- |
| Paint stability* | good | poor |
| Dry Time | Excellent | Excellent |

*paint stability is measured after heating for 10 days at 140° F. If the KU viscosity has increased by more than 10 units, the paint stability is poor.

Aqueous coating composition 44-1 of the invention containing PNPs provides a better balance of aqueous coating properties relative to those of the comparative composition 44-2.

EXAMPLE 45

Freeze/Thaw Stability of Aqueous Coating Composition

A semigloss latex paint is made. Pigmentation is TI-PURE™ R-706 and RHOPLEX™ Ultra, thickener is ACRYSOL™ RM-2020NPR, and coalescent is 9% TEXANOL™ by weight based on polymer solids. The volume solids (VS) is 33.9% and the pigment volume concentration (PVC) is 25.8%. The paint is found to fail one freeze/thaw cycle, and to become coagulated and unusable after thawing from one cycle of freezing.

The addition of PNPs consisting of 70 wt % MMA, 20 wt % AA, and 10 wt % TMPTA at a level of 3% PNP by wt based on paint solids by weight, is found to improve freeze/thaw stability of the paint to pass 5 cycles of freezing and thawing without significant change in viscosity or gloss level of cast films of the paint.

What is claimed is:

1. An aqueous composition comprising a pigment, an aqueous dispersion of polymeric nanoparticles having a mean diameter of from 1 to 50 nanometers, said nanoparticles including amine functionality and further including, as polymerized units, at least one multi-ethylenically-unsaturated monomer; selected from the group consisting of divinyl benzene, trivinylbenzene, divinyltoluene, divinylpyridine, divinylnaphthalene, divinylxylene, ethyleneglycol di(meth)acrylate, trimethylolpropane tri(meth)acrylate, diethyleneglycol divinyl ether, trivinylcyclohexane, allyl (meth)acrylate, diethyleneglycol di(meth)acrylate, propyleneglycol di(meth)acrylate, 2,2-dimethylpropane-1,3-di(meth)acrylate, 1,3- butylene glycol di(meth)acrylate, 1,4-butanediol di(meth)acrylate, 1,6-hexanediol di(meth)acrylate, tripropylene glycol di(meth)acrylate, triethylene glycol di(meth)acrylate, tetraethylene glycol di(meth)acrylate, polyethylene glycol 200 di(meth)acrylate, polyethylene glycol 600 di(meth)acrylate, ethoxylated bisphenol A di(meth)acrylate, poly(butanediol) di(meth)acrylate, pentaerythritol tri(meth)acrylate, trimethylolpropane triethoxy tri(meth)acrylate, glyceryl propoxy tri(meth)acrylate, pentaerythritol tetra (meth)acrylate, dipentaerythritol monohydroxypenta(meth)acrylate, divinyl silane, trivinyl silane, dimethyl divinyl silane, divinyl methyl silane, methyl trivinyl silane, diphenyl divinyl silane, divinyl phenyl silane, trivinyl phenyl silane, divinyl methyl phenyl silane, tetravinyl silane, dimethyl vinyl disiloxane, poly(methyl vinyl siloxane), poly(vinyl hydro siloxane), poly(phenyl vinyl siloxane), and mixtures thereof, an anionically-stabilized emulsion polymer having a mean diameter of greater than 50 nanometers; and a volatile base in an amount sufficient to deprotonate the amine.

* * * * *